United States Patent [19]
Hall

[11] Patent Number: 5,611,805
[45] Date of Patent: Mar. 18, 1997

[54] METHOD AND DEVICE FOR DETERMINING PLACEMENT OF KERATOTOMY INCISIONS

[76] Inventor: Gary W. Hall, 2501 N. 32nd St., Phoenix, Ariz. 85008

[21] Appl. No.: 433,862

[22] Filed: May 2, 1995

Related U.S. Application Data

[63] Continuation-in-part of Ser. No. 151,273, Nov. 12, 1993, Pat. No. 5,411,511.

[51] Int. Cl.$^6$ ........................................ A61F 9/00
[52] U.S. Cl. .................... 606/166; 606/170; 606/172
[58] Field of Search ...................... 606/166, 170, 606/172, 167; 83/522.14, 522.12, 522.26, 522.11

[56] References Cited

U.S. PATENT DOCUMENTS

| | | | |
|---|---|---|---|
| 4,178,820 | 12/1979 | Gerber | 83/13 |
| 4,200,015 | 4/1980 | Gerber | 83/22 |
| 4,543,867 | 10/1985 | Ichikawa | 83/502 |
| 4,637,393 | 1/1987 | Ray | 128/305 |
| 4,665,914 | 5/1987 | Tanne | 128/305 |
| 4,674,503 | 6/1987 | Peyman et al. | 606/166 |
| 4,750,489 | 6/1988 | Berkman et al. | 128/314 |
| 4,943,296 | 7/1990 | Funakubo et al. | 606/166 |
| 5,071,427 | 12/1991 | Stahl | 606/172 |
| 5,222,967 | 6/1993 | Casebeer et al. | 606/166 |
| 5,308,355 | 5/1994 | Dybbs | 606/166 |

FOREIGN PATENT DOCUMENTS

| | | | |
|---|---|---|---|
| 1337045 | 9/1987 | U.S.S.R. | 606/167 |

OTHER PUBLICATIONS

"Introduction to Biomechanics of the Cornea" by Kurt A. Buzard, MD, FACS, Retractive & Corneal Surgery, vol. 8, Mar./Apr. 1992, pp. 127-138.

Primary Examiner—Michael Powell Buiz
Assistant Examiner—Kevin Truong
Attorney, Agent, or Firm—Cahill, Sutton & Thomas P.L.C.

[57] ABSTRACT

A keratotomy incision is formed in a cornea by manipulating an RK knife so that its blade extends a preselected depth into a point on the cornea. Sufficient force is applied by a surgeon's fingers to the knife to advance its blade in a preselected direction. Advancement of the blade is halted when resistance of the cornea against the blade exceeds a certain level. In one embodiment, a plurality of such incisions are formed in a predetermined pattern until a final incision is made wherein resistance of the cornea against the leading edge of the blade exceeds the particular level at the starting point for that final incision. The blade then is withdrawn from the cornea, whereby the plurality of incisions reduce strain in collagen fibrils of the cornea so as to correct a refractive error associated with such strain.

14 Claims, 4 Drawing Sheets

METHOD AND DEVICE FOR DETERMINING PLACEMENT OF KERATOTOMY INCISIONS

CROSS REFERENCE TO RELATED APPLICATION

This application is a continuation-in-part of my allowed pending patent application "METHOD AND DEVICE FOR DETERMINING PLACEMENT OF KERATOTOMY INCISIONS", Ser. No. 08/151,273 filed Nov. 12, 1993, now U.S. Pat. No. 5,411,511.

BACKGROUND OF THE INVENTION

The invention relates to a method of determining the extent or length of a keratotomy incision by determining a point of increased resistance against blade advancement of an RK knife as it makes the incision. The incision is stopped when a critical level of resistance is detected. The resulting incision length optimally corrects the patients vision, which is believed to occur as a result of minimizing strain within collagen fibrils of the corneal stroma, which strain is associated with refractive errors that produce a visual impairment requiring correction.

Ophthalmologists usually use "optical zone markers" to determine the length of a keratotomy incision. With the Fyodorov (Russian) technique, a radial RK incision typically begins approximately one millimeter from the outer edge of the cornea. The blade of an RK knife is moved radially inward toward an "optical zone mark" (which is a shallow indentation previously made in the epithelium by the surgeon around a central area of the cornea by pressing a stainless steel device known as a zone marker against the central cornea). An astigmatic keratotomy (AK) incision is performed by making the incision(s) tangential to the steepest radial curvature of the cornea in a linear or curvilinear fashion at a predetermined optical zone. The size of the optical zone marker usually is determined according to nomograms or empirical formulas based on age, sex, degree of correction needed, thickness, curvature, and/or diameter of the cornea. However, such nomograms or empirical formulas are based on averages for a large number of patients, and are not necessarily accurate for a particular patient if his or her eye has "non-average" material (i.e., tissue) properties.

Such nomograms typically are based on the response of a 30 year old caucasian having an intraocular pressure of 15 millimeters of mercury and little or no astigmatism. Typically, surgeons use "fudge factors" on data from such nomograms to develop an RK surgical plan for individuals differing from the typical 30 year old caucasian on which the nomograms are based. However, some patients may have exceptionally high corneal elasticity, or exceptionally low intraocular pressure, in which case even such "fudge factors" are likely to produce inaccurate results. When nomograms are used to design a surgical plan for radial keratotomy for such patients, there typically will be a large number of "undercorrections" of refractive errors. Since "overcorrections" are more difficult to surgically correct or "enhance" than undercorrections, most nomograms are weighted toward producing undercorrection. Therefore, later "enhancement" surgery is required in a high percentage of patients.

Mathematical predictions of the effect of proposed incisions on the cornea may be computed instead of (or in addition to) using nomograms to aid in preparing a surgical plan for radial keratotomy. The primary analytical tool used for this purpose is a "finite element analysis" (FEA) executed by means of a computer program. Instead of attempting to predict the effect of an incision on the entire surface of the cornea, such surface is subdivided into small "finite elements". After making certain assumptions about the biomechanical properties of a given cornea, both measured and nonmeasured data are applied to differential equations used in the FEA software, and the effect of the incisions on each of the finite elements "summed" across the entire cornea is determined. This helps predict the change of the corneal surface shape resulting from the proposed incisions.

FEA models of the cornea which have been described in the literature inherently depend on accurate determination of the biomechanical properties, some of which are not as yet accurately measurable. Furthermore, some assumptions regarding biomechanical properties of the cornea may not be accurate for an FEA model. Modeling of the effect of proposed incisions to develop a surgical plan for each patient by FEA models probably is not yet practical.

There is an unmet need for a technique for further optimizing lengths and number of keratotomy incisions based primarily on the material properties of the cornea and its behavior in immediate (acute) response to making of such incisions.

There also is an unmet need for a technique for minimizing strain in collagen fibrils of a cornea in such a way as to correct refractive impairment thereof.

There also is an unmet need for a way to reliably correct refractive errors with keratotomy on patients for whom techniques that rely on nomograms or empirical formulas do not produce accurate results.

SUMMARY OF THE INVENTION

Accordingly, it is an object of the invention to provide a method for placement of keratotomy incisions (to correct refractive errors) based primarily on the material properties of the cornea.

It is another object of the invention to provide a radial keratotomy knife adapted to aid in optimal placement, length, depth, and number of incisions for correction of refractive errors, including myopia, astigmatism, hyperopia and/or combinations thereof.

It is another object of the invention to provide a way of optimally reducing strain within the corneal collagen to improve vision.

It is another object of the invention to provide increased accuracy in the subsequent correction of undercorrected or overcorrected surgical or laser procedures to correct myopia, hyperopia, and/or astigmatism by detecting optimal placement, length, depth, and number of keratotomy incisions required to correct residual refractive error.

Briefly described, and in accordance with one embodiment thereof, the invention provides a method of making an incision in a cornea by manipulating an RK (radial keratotomy) knife so that its blade extends a preselected distance into the cornea at a preselected point thereof. Sufficient force is applied to the RK knife to advance the blade in a preselected direction. Movement of the blade is halted to complete the incision when resistance of the cornea against the blade exceeds a critical level. In one embodiment of the invention, a plurality of incisions are formed in a predetermined pattern in the foregoing manner until a final incision is made wherein resistance of the cornea against the leading edge of the blade exceeds the particular level at the starting point for that final incision. The blade then is withdrawn from the cornea, whereby the plurality of incisions relieve strain in collagen fibrils of the cornea so as to correct a refractive error associated with such strain. In one embodiment of the invention a surgeon uses an RK knife with sufficiently low friction that the surgeon is able to feel the critical resistance and stop the incision accordingly. In another embodiment of the invention, the amount of force applied by the surgeon's fingers to a body of the RK knife produces a signal representative of the force. The signal indicates the level of resistance of the cornea against a leading edge of the blade. The level of the resistance is displayed on a computer screen and/or is audibly indicated. In another embodiment, the blade is supported on an elastic member. The counterforce produced by resistance of the cornea against the leading edge of the blade is indicated by producing a signal representing the amount of elastic deformation of the elastic member. In another embodiment, movement of the blade is halted when stria of predetermined prominence, shape, and/or orientation are observed on a surface of the cornea immediately ahead of the blade.

DETAILED DESCRIPTION OF THE PREFERRED EMBODIMENTS

As I performed various procedures to correct myopia and/or astigmatism through incisional keratotomy using a relatively new, exceptionally thin blade, I realized that the blade could be advanced very easily through the corneal stroma, compared to advancement of the thicker, more conventional blades I had previously used. Such previous blades had pointed tips, and were approximately 150 micrometers thick. I requested a blade manufacturer to develop a thinner blade. The result was a new Thornton blade 80 micrometers in thickness, with a squared tip. The trailing edge of the squared tip was inclined 18 degrees relative to the leading edge.

To my surprise, for each advancement of the blade to form a keratotomy incision a "resistance point" was reached in the cornea. I realized that the blade would not pass beyond the resistance point without considerably increased exertion.

I continued to experiment, and discovered that even within the same cornea some of the resistance points (which I found to occur in both astigmatic and radial incisions) were located before preestablished optical zone markers, and other such resistance points were located beyond the optical zone marker. Using these resistance points, rather than the optical zone markers, as a guide for determining the incision lengths, I discovered that different length incisions frequently would occur on the same cornea, some shorter than indicated by the optical zone marker and others longer. I also noticed that the new Thornton type blade typically could be advanced more easily through the stroma of patients who had a higher magnitude of nearsightedness and astigmatism.

Figure 2:
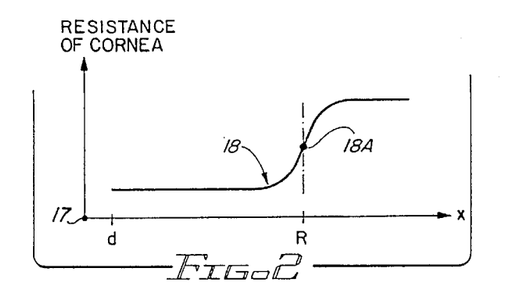
FIG. 2 is a diagram of resistance of the cornea against a leading edge of a radial keratotomy blade, while making an incision.

The graph of FIG. 2 qualitatively illustrates the amount of force applied to an RK knife as the incision is being made in the direction x. Numeral 17 designates the outer edge of the cornea 10, and the solid line 18 indicates the amount of force being applied to advance the blade. At point R the force required to advance the blade increases abruptly, as indicated by 18A. My experimental results indicate that this point corresponds to the transition between strained and relaxed corneal fibrils.

Initially, I was unable to provide a plausible explanation for the resistance points. I considered various possible effects of blade tilt, bunching of the epithelium against the RK knife, compaction of collagen by establishment of optical zone markers, and corneal surface irregularity as causes of the resistance points. I eventually ruled these out as causative factors as a result of my further observations. I asked a few other ophthalmologists if they had recognized such resistance points, but none could identify with what I was observing.

I continued to experiment with the technique of stopping the incision at the resistance points rather than at the optical zone markers because I discovered that the new technique seemed to produce better correction, with far fewer significant overcorrections or undercorrections than when the optical zone markers based on empirical nomograms were strictly adhered to in order to determine each incision length.

Figure 4:
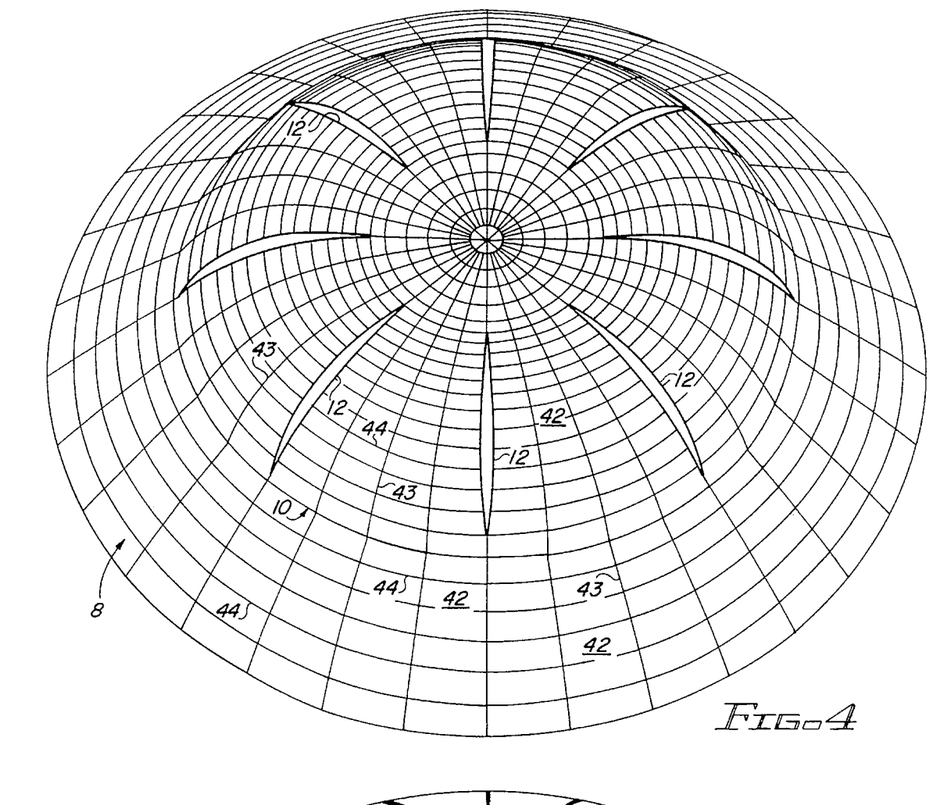
FIG. 4 is a perspective view of a finite element analysis model of an eye having a plurality of RK incisions in the cornea.

My attempts to develop a theory to explain the occurrence of the above resistive points are partly based on information regarding stress/strain relationships computed for a cornea with RK incisions therein using a finite element analysis (FEA) model. FIG. 4 shows a diagram of the surface of cornea 10. (The terms "stress" and "strain" have the following common meanings. The stress is equal to the amount of load force applied to a material divided by the cross sectional area thereof. The strain is the change in length or deformation of the material due to the load force divided by the "original" length of the material. Young's modulus is the ratio of the stress to the strain. See "Introduction to Biomechanics of the Cornea" by Kurt A. Buzard, M.D. published in "Refractive & Corneal Surgery", Volume 8, March/April 1992, page 127.) Numeral 42 designates the finite elements of the model, each of which is bounded by adjacent "radial" lines 43 and two adjacent "equatorial" lines 44. Eight RK incisions 12 have been included in the illustrated model. The FEA model used to generate FIG. 4 was found to accurately represent a patient's eye having the same material properties as those used in the model.

Figure 1:
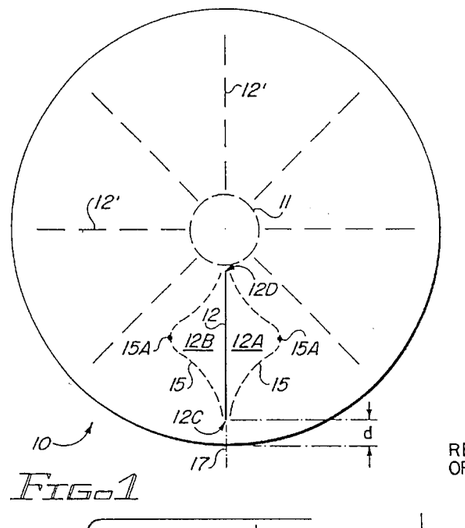
FIG. 1 is a plan view diagram useful in explaining the theory of the present invention.
Figure 5:
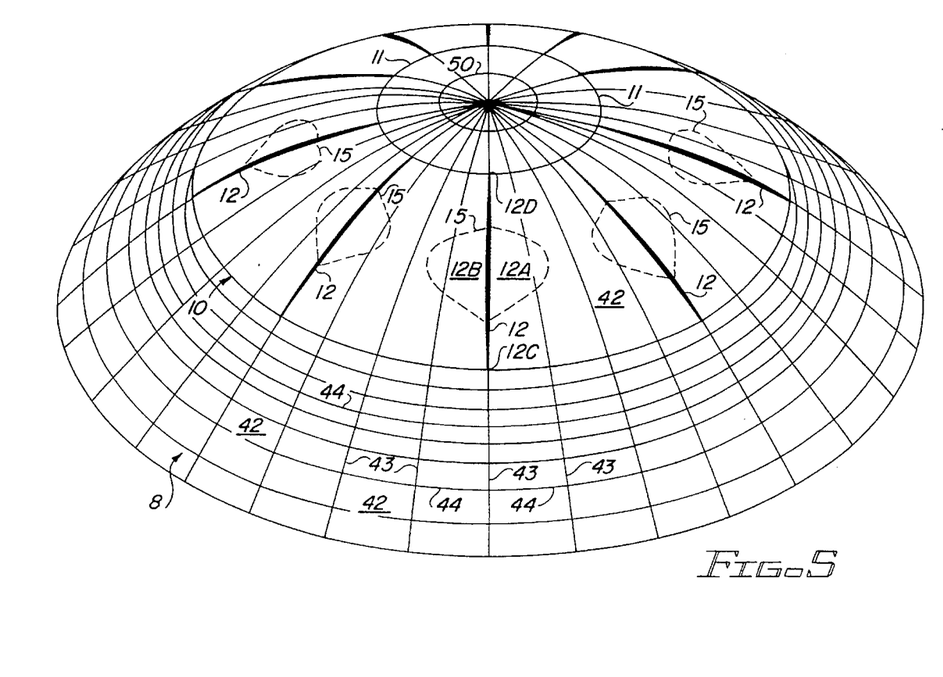
FIG. 5 is a perspective view similar to FIG. 6 with areas of different levels of strain indicated thereon.

FIG. 5 shows a scale diagram of the surface of an eye as traced from a display computed by the same FEA model as FIG. 4, and further indicates the computed strain in the epithelium throughout the sclera and cornea 10. The display referred to was a color display, the colors in various areas indicating the computed strain level thereat. The highest levels of strain were indicated by red color within the central area 50. Lower levels were indicated by a yellow band between area 50 and the zone indicated by 11. The band between the outer boundary of cornea 10 and zone 11 had several lower strain levels indicated by several shades of blue, respectively. The lowest levels of strain occurred in the material in the regions bounded by dotted lines 15 along the central side portions 12A and 12B of modeled incisions 12 (as also indicated above in FIG. 1). In the original computer display, regions 15 appeared as a very dark blue color. The lowest strain regions 15 were included in a generally annular low strain band shown in the original display as a different, lighter shade of blue. The sclera 8 appeared as a yellow band, with high levels of computed stress in the surface material represented by the corresponding FEA elements 42.

FIG. 5 thus shows that the lowest strain points occur alongside of the incision 12.

Figure 3A:
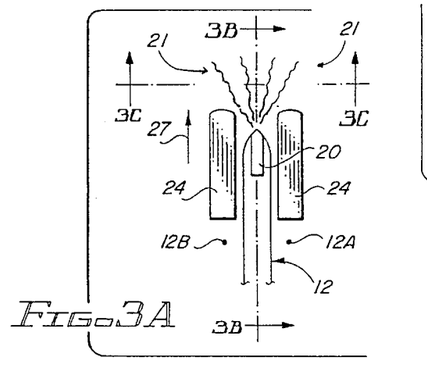
FIG. 3A is a plan view illustrating a phenomena causing increased resistance to advancement of the radial keratotomy knife as strain in the cornea is reduced along the sides of the incision.

I observed that folds or stria 21 appear in a triangular pattern on the surface of the epithelium just ahead of the leading edge of blade 20 of the RK knife just as the sharp increase in resistance to blade 20 occurred. The cross sectional view shown in FIG. 3C along section lines 3C—3C of FIG. 3A illustrates the stria 21, and FIG. 6 perhaps best illustrates the appearance of the stria 21.

The strain information in FIG. 5 led me to recognize that as the strain at the inner tip 12D of the incision suddenly changes, the blade 20 would no longer easily advance through the epithelium. (The increase in force is definitely made more noticeable when mechanically thin diamond blades are used, because they create less friction.) The stress/strain distribution computed using the finite element analysis model shows minimum strain in the cornea material along the sides 12A and 12B of incision 12 (FIG. 3A).

Figure 1A:
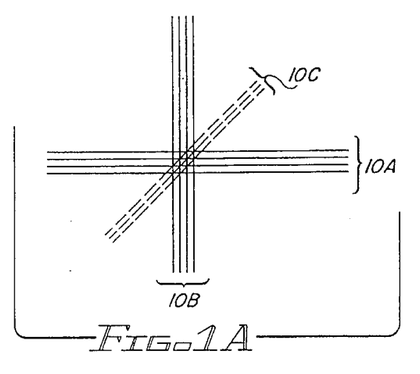
FIG. 1A is a diagram of a cross section of a corneal incision, and is useful in describing the theory of the present invention.

As indicated in FIG. 1A, the stroma of cornea 10 is comprised of a number of parallel layers of lamellae that includes bundles of parallel collagen fibers. The bundles of the various layers are approximately 2.5 microns thick, and run in various directions. In FIG. 1A, numeral 10A designates a bundle of lamellae fibers in one layer, running in a direction parallel to the page. Numeral 10B designates bundles in an adjoining layer running in a direction perpendicular to bundle 10A, and numeral 10C designates bundles of lamellae in yet another layer running obliquely to the directions of fibers 10A and 10B. There are enough lamellae fibers running in different directions at any point in the cornea that an incision being made in virtually any direction against "relaxed" fibrils will experience the "bunching" and resistance that causes the stria 21 illustrated in FIGS. 3A, 3C, and 6. Apparently, such bunching occurs as a result of the increased number of relaxed fibrils in front of the blade.

My experiments and the development of my theory as of the date of filing my above mentioned parent patent application seemed to indicate that when the stress/strain relationships in the cornea reach an optimum "equilibrium" or "low" point, the resistance force reaches the above mentioned critical level, beyond which "excessive" force is required to continue advancing the RK knife. If the RK knife is advanced beyond that point, possibly a loss of "equilibrium" of the stress/strain relationships occurs, and more strain is introduced into the central fibrils of the cornea.

The most unexpected result observed from my experiments is that the above mentioned critical resistance points seem to correspond with optimal visual correction, i.e., the point at which emmetropia is achieved. There appears to be a "natural point", i.e., an equilibrium point, associated with perfect vision, i.e., emmetropia For "ametropia" or abnormal refractive conditions, the strain in the cornea appears to be abnormally high in certain fibrils. Stated differently, the results of my experiments to date have led me to believe that the condition of emmetropia may be closely related to achieving the lowest overall possible strain in a particular cornea, and that the degree of ametropia is proportional to the degree of abnormal strain leading to the myopia, astigmatism, or hyperopia condition being corrected.

If enough incisions are stopped precisely at the critical resistance points, then optimum vision should be achieved for the particular patient. The increased accuracy can be attributed to the fact that the incisions are being made as a function of the ocular material behavior of the present cornea, rather than being based on average empirical formulas or nomograms. I now use the conventional optical zone markers merely as a general indicator of the approximate desired incision length, but I rely on the critical resistance point to actually determine the length of each incision.

The reliability of the above described technique makes it possible to avoid the necessity for a surgeon to make keratotomy incisions as deep as possible, and therefore reduces the occurrences of perforations. In addition, reduction of significant overcorrection or undercorrection of refractive errors also reduces the need for subsequent surgical procedures. Furthermore, as each incision is made, each new critical resistance point also incorporates the effect of previously placed incisions and possibly other factors that affect stress/strain relationships in that eye, such as intraocular pressure.

My further observations of the above described resistance point phenomenon have led me to develop a "corneal collagen strain theory" of ametropia. This strain theory is based on my observation that if a corneal fibril (or any elastic fibril) is under tensile strain, that fibril is more easily cut than if it is in a relaxed condition. I now believe that when I feel or sense the increased resistance on the blade of an RK knife as an incision 12 is being made, such increased resistance indicates a transition of the cutting edge of the RK knife blade from a region in which fibrils oriented perpendicularly or obliquely to the direction of the incision are under excessive strain (which is associated with the myopia or astigmatism to be corrected) to a region in which similarly oriented fibrils are more relaxed or are under no strain.

At such a transition point, the above mentioned stria 21 immediately appear on the epithelium, emanating from the cutting edge of the RK diamond blade in a generally triangular pattern. Apparently, a fibril which is under strain (and therefore is lengthened over its relaxed state) cuts more easily in a direction perpendicular to the axis of the strained fibril than if the same fibril is in its relaxed state, just as strands of a net would be more easily transversely cut when taut than when relaxed. Of course, the cutting edge of the RK knife must be sufficiently sharp and must be configured so as to allow the surgeon to actually feel or associate the difference in resistance against the blade of the RK knife between strained fibrils and the relaxed fibrils of the epithelium. Apparently, the magnitude of the ametropia (e.g., the extent of myopia or astigmatism) is generally proportional to the magnitude of the strain within the fibrils, which strain apparently is associated with the ametropic condition.

The location of the strain associated with myopia is in the peripheral cornea. This can be understood by referring to Fig. 11, which indicates the parallel fibrils in one of the approximately 200 layers of corneal collagen of the stroma. The "peripheral cornea" is referred to as the part of cornea 10 outside of boundaries 51 and 52, which are tangential to optical zone 11. The fibrils in the "peripheral cornea" are referred to as "peripheral fibrils" 46A. The fibrils 46B in the "central cornea" between boundaries 51 and 52 are referred to as "central fibrils" 46B. Peripheral collagen fibrils 46A are cut most easily along a radial direction perpendicular to strained peripheral fibrils 46A.

Figure 11:
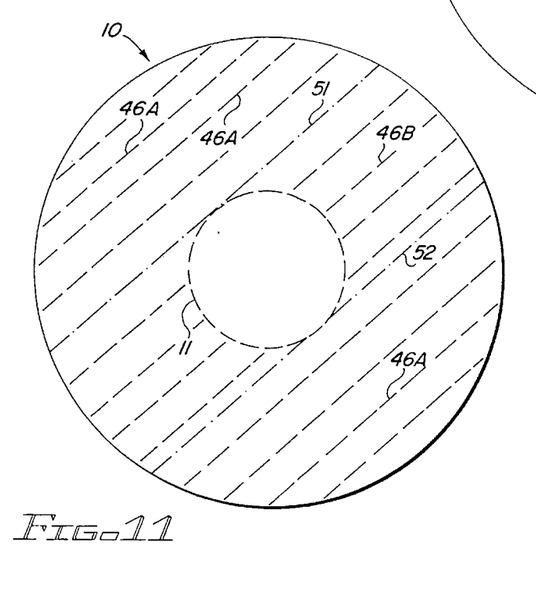
FIG. 11 is a plan view diagram of the cornea useful in explaining the invention.

The location of the increased strain that produces astigmatism and hyperopia is in the central region containing central fibrils 46B. In hyperopia (farsightedness), the strain directions within the various 2.5 micron layers of corneal collagen are uniformly distributed 360 degrees around the cornea. With astigmatism, the central fibrils 46B oriented in the steepest corneal meridian are under excessive strain. In hyperopia and astigmatism, the fibrils are cut most easily in a tangential plane perpendicular to the centrally oriented fibrils under strain.

According to my theory, all of the collagen fibrils in the emmetropic cornea are in their most relaxed states. It follows that the treatment of ametropia involves optimally reducing all of the strain where excessive strain exists in such fibrils in order to produce an emmetropic condition. One method of achieving this result is by strategically placing incisions, the terminal end points of which are located at higher resistance points, which in turn are located at points of lower strain in the collagen fibrils.

It should be understood that the above described refractive adjustment procedures do not necessarily produce a permanent perfect correction, because after the initial incisions, the cornea undergoes "re-equilibration" of strain (subacute change) within the collagen fibrils. Such re-equilibration usually occurs over a period of several weeks to several months, during which additional strain may be reintroduced into some of the fibrils, effectively undoing some of the corrective effect of the original incisions. The cornea is composed of viscoelastic material comprised of approximately 80 percent water and the above mentioned bundles of elastic collagen which account for essentially all of its structural properties. Such bundles of elastic collagen run in layers of approximately 2 to 2.5 microns thickness and are oriented in one direction in each layer, also may exist under varying amounts of strain. The magnitude of strain in an elastic fibril is defined by its length when stretched or "under load" divided by its length in a relaxed or nearly relaxed state. When an elastic fibril such as a collagen fiber in a strained condition is cut, the strain within that fibril is immediately reduced toward its "relaxed" or "no strain" state. Each subsequent incision cuts through fibers in which the strain already has been reduced by a previous incision. Each such subsequent incision further reduces strain in all fibers of the cornea, but by lessening amounts.

Further strain may develop in the fibrils over a period of years, apparently caused by mechanical stresses applied to the cornea and leading to progressive hyperopia and/or slow shifts in astigmatism. Since these changes in the cornea are not accurately predictable, incisional refractive surgery can never be considered to be "perfect".

Emmetropia occurs when all fibrils of the cornea are in their most relaxed state. As explained above, in a myopic condition the orientation of excessive strain within the collagen fibrils is in the peripheral cornea, and the amount of myopia is generally proportional to the amount of excessive strain in the peripheral fibrils 46A (FIG. 11). (As mentioned above, the fibrils of the approximately two hundred 2.5 micron thick layers of corneal collagen are uniformly parallel within each layer, the various layers being oriented in many directions, respectively.) Incisions made in a radial direction perpendicular to such peripheral fibrils 46A are cut reducing the strain within the fibrils as the surgeon passes the sharp diamond blade from the limbus 11 toward the center of the cornea, with the blade passing easily through the strained fibrils. When the blade reaches a point where the corneal fibrils are relaxed, the above mentioned sudden increase in resistance to further passage of the blade occurs, and the epithelial stria 21 emanate from the diamond cutting edge. Generally, the greater the amount of myopia, the longer each incision is required before the resistance point is reached.

The first incision in the cornea has the effect of reducing peripheral strain circumferentially, but non-uniformly, around the entire cornea. The greatest amount of strain reduction occurs on either side of the midpoint of the incision and the minimum amount of strain reduction occurs at the point midway between two incisions.

The initial incisions should be made on opposite sides of the optical zone. The first group, shown in FIG. 9 by dashed lines 12-1,2 . . . 8, all are begun at an outer starting point A on the limbus 16 of cornea 10, and each is continued radially toward the center of cornea 10 to a resistance point B at which the sudden increase in resistance is sensed. The initial group of incisions 12-1,2 . . . 8 generally are of the same length, although some of the resistance points B may be outside of a cautionary optical zone marker 11, as shown. For example, the resistance points B of incisions 12-1,2,3,4 are located outside of optical zone marker 11, while resistance points B of incisions 12-5 and 12-6 are located inside optical zone marker 11.

Then, a second set of radial incisions 14-1,2,3 . . . are made, each being started at a point A on limbus 11 and continuing to an inner resistance point B. Generally, most of the incisions of the second group are of approximately the same length, until suddenly the resistance point B of one such incision is detected immediately after that incision is begun on limbus 16, i.e., as soon as the tip of the RK blade is forced into the epithelial tissue. For example, in FIG. 9, incision 14-6 has its resistance point B much closer to limbus 11 than the previous incisions 14-1,2 . . . 5. The resistance point B of the final incision made in cornea 10 occurs at the same location as its starting point, as indicated by 14-7A,B. I have used the foregoing procedure successfully for correction of myopia for 6000 eyes in recent months.

Figure 9:
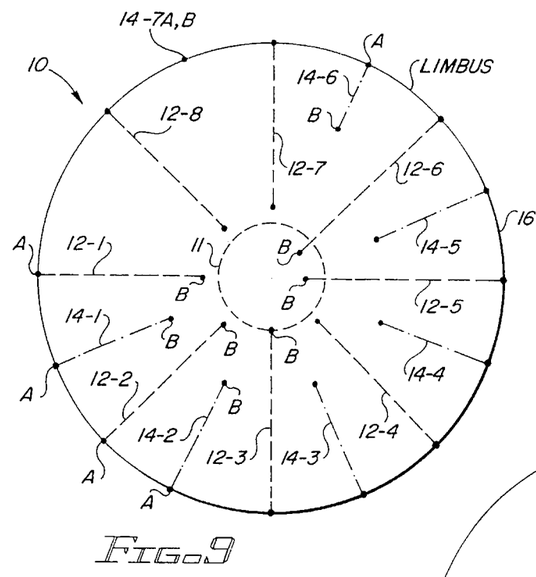
FIG. 9 is a plan view diagram useful in explaining the making of a secondary group of radial incisions, after first making a primary group thereof, so as to produce a final "resistance point" that occurs at the limbus of the cornea.

If my strain theory is correct, at this point all of the collagen fibrils in cornea 10 are near or at their most relaxed conditions and the patient's myopia usually is completely or nearly corrected when the resistance point of the last radial incision occurs at the beginning of that incision. However, a new but lesser myopic condition may be reintroduced as strain reenters the peripheral fibrils during equilibration and some further correction is likely to be needed.

There is no way of knowing how may incisions will be required before a resistance point B coincides with the starting point A of a final incision, thereby indicating that relaxation of all collagen fibrils has been achieved. Increasing the number of initial radial incisions such as 12-1,2 . . . 8 before beginning the second group such as 14-1,2 . . . increases the risk of certain undesirable complications such as instability of the correction, but has the advantage that the incisions are shorter and consequently the clear optical zone is larger. I believe that the minimum size of the optical zone 11 should be approximately 20 millimeters in an accurately placed mark of the corneal intercept to reduce the "glare disability" frequently associated with radial keratotomy. Since correction of higher degrees of myopia generally requires more incisions and also requires that the incisions be longer, the patient must take more risk of undesired complications, including instability of the correction and glare disability, to achieve full correction.

Although use of optical zone marker 11 is not essential, I prefer to use it as a guide to provide reassurance that the resistance point B of each incision is reached near the vicinity of the optical zone marker 11, provided optical zone marker 11 is accurately positioned. By using an ACULA-SER device (developed by Dr. Clifford Terry) including a helium neon laser attachable to an operating microscope, the corneal intersect of the visual axis can be determined, and the optical zone marker 11 should be accurately positioned about it.

Even though emmetropia or near emmetropia (i.e., full correction) usually is achieved at the time of the initial RK surgery, additional strain introduced during the first months of healing usually necessitates slight lengthening of the existing incisions to new resistance points B or adding of a few new incisions as described above to reestablish the emmetropic condition.

Figure 10:
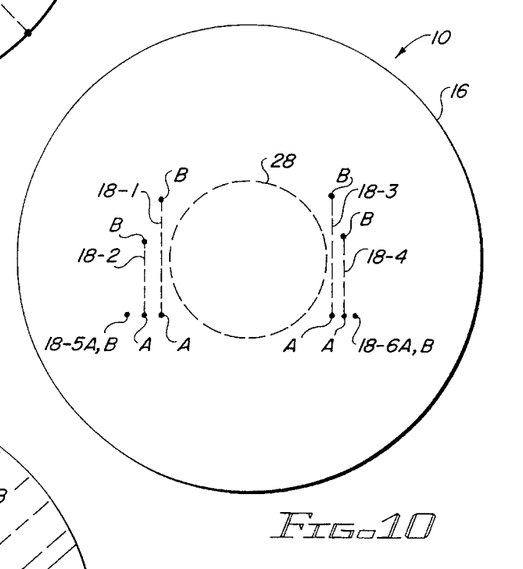
FIG. 10 is a plan view diagram useful in explaining a procedure for making incisions the lengths of which are determined by occurrence of resistance points, so as to minimize strain in collagen fibers associated with corneal astigmatism.

In FIG. 10, dotted lines 18-1 through 18-4 and points 18-5A,B and 18-6A,B represent incisions made in a cornea 10 to correct an astigmatism that is designated by dashed lines 28. A first incision 18-1 is begun at starting point A, which is selected on the basis of the surgeon's determination of the location of a suitable starting point. The RK knife is moved in the direction tangential to the steepest slope portion of astigmatism 28 until a sudden increase in resistance is experienced, at point B. Then, a second incision 18-2 is made parallel to incision 18-1, continuing from its starting point A until a substantially increased resistance point B thereof is detected. Starting point A of incision 18-2 may be located approximately 1 millimeter from point A of first incision 18-1 as shown. This procedure is repeated until a resistance point B of an incision coincides with the starting point A of that incision, for example as indicated by incisions 18-5A,B.

Then, the same procedure is repeated on the opposite side of astigmatism 28 to form incisions 18-3, 18-4, and 18-6A, B, at which point strain has been eliminated or nearly eliminated in all of the fibrils associated with or causing astigmatism 28.

Although the results of my experiments indicate that I have been able to "feel" the resistance point with reasonable accuracy to optimally terminate each incision, it would be highly desirable to provide an RK knife that includes a way of automatically sensing the increased resistance level at which the present incision should be stopped.

Figures 6, 7:
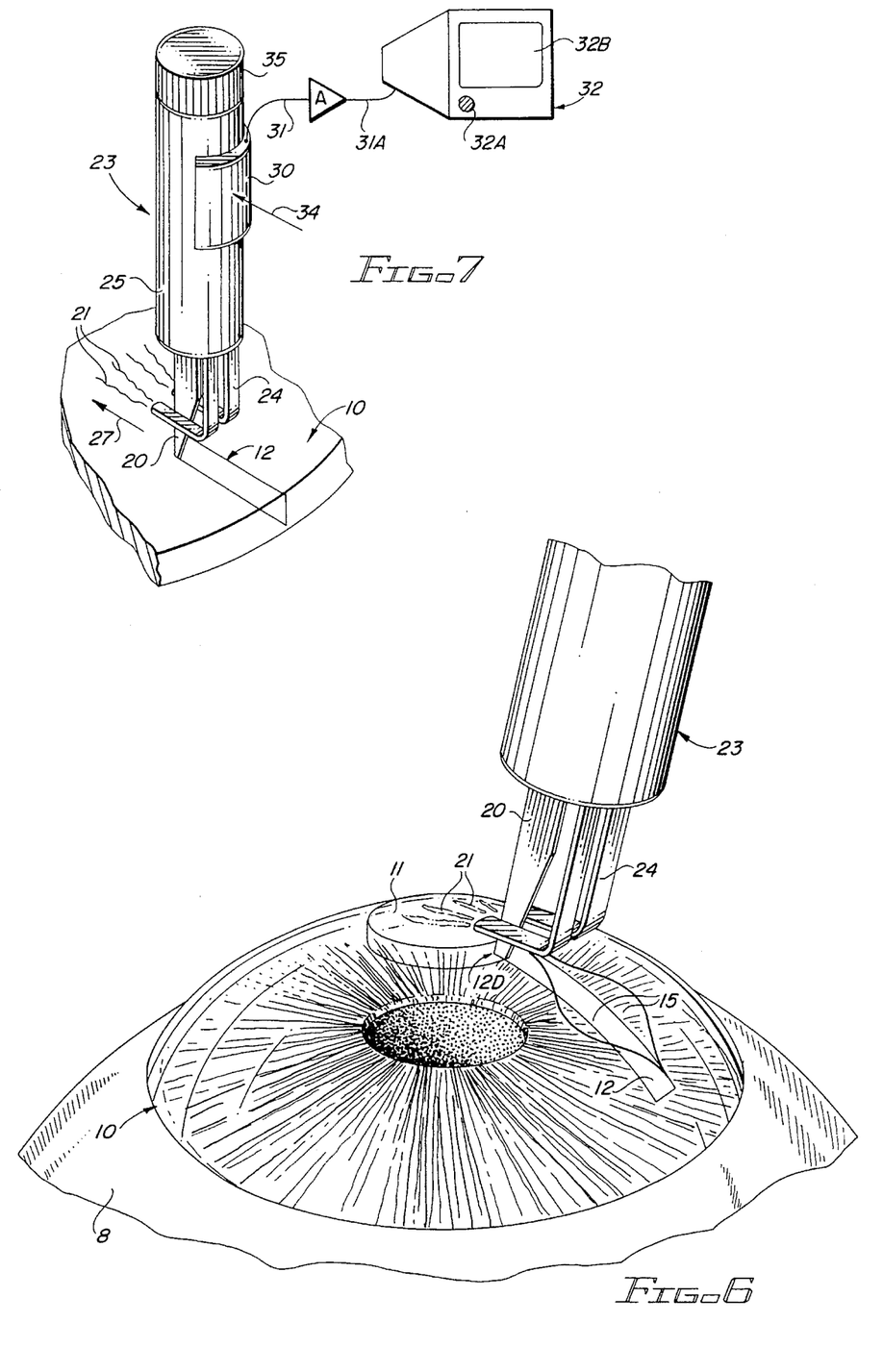
FIG. 6 is a perspective view illustrating the making of a keratotomy incision, with areas of high and low strain in the cornea indicated, and "bunching" or folding to form stria in the epithelium beyond the RK knife.
FIG. 7 is a perspective view of one embodiment of a radial keratotomy knife adapted to sense resistance to advancement of the knife making a radial keratotomy incision.

FIG. 7 shows one approach to designing such an RK knife. RK knife 23 includes a conventional body 25 and micrometer adjustment 35 that adjusts the depth of the lower tip of blade 20 relative to the bottom surfaces of each foot 24 (which slides along the cornea surface as the incision is made). Arrow 27 indicates the direction of advancing blade 20 as the incision 12 is being formed. A pressure or strain measuring device 30 is affixed to or incorporated in the surface of the body 25 of RK knife 20, and produces signals on conductors 31 indicating how much pressure the surgeon is applying to advance blade 20 through the cornea. That information is communicated, either by wires 31 and an amplifier or by an RF or infrared communication coupling, to a computing device 32 which analyzes that information and produces a graphic and/or audible output immediately indicating to the surgeon when the critical resistance point has been reached.

Figures 3B, 8:
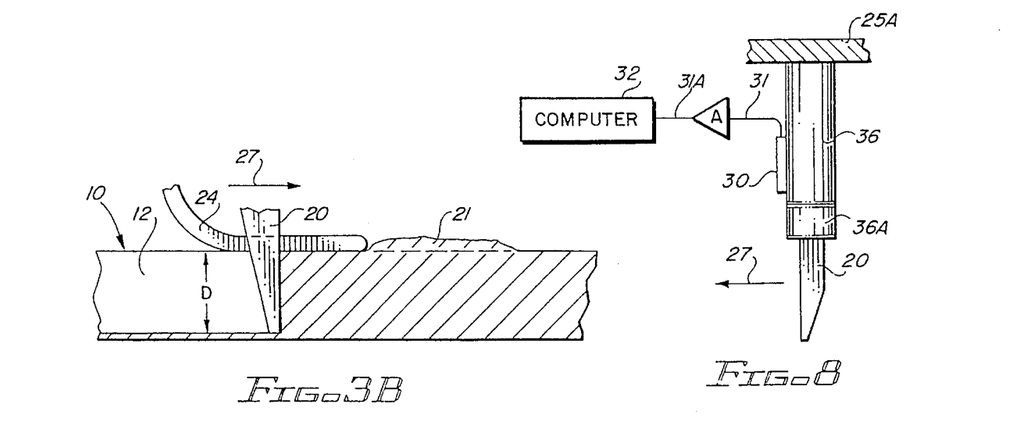
FIG. 3B is a sectional view taken along section line 3B—3B of FIG. 3A.
FIG. 8 is a perspective view of another embodiment of a radial keratotomy knife adapted to sense resistance imparted to the blade as it advances to form a corneal incision.
Figure 3C:
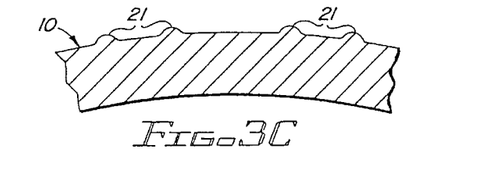
FIG. 3C is a sectional view taken along section line 3C—3C of FIG. 3A.

FIG. 8 discloses another embodiment, in which the blade 20 is mounted on the end of an elastic elongated support 36, the upper portion of which is anchored firmly in the upper portion of the RK knife body (not shown). As pressure is applied to the body of the RK knife by the fingers of the surgeon, the elongated elastic member 36 flexes by an amount proportional to the resistance that the cornea exerts against the leading edge of blade 20. A strain gauge 30 is adhesively or otherwise attached to the surface of elastic member 36 and generates a corresponding electric signal 31 that indicates the amount of flexing and hence the amount of resistance the cornea applies against advancement of blade 20. Signal 31 may be applied to an input of an amplifier included within or external to body 25. The amplifier output is coupled, either by means of conductors or a wireless communication link, to computing device 32. Computing device 32 generates graphic and/or audible information that indicates the amount of resistance of collagen at the front edge of the incision 12 against the leading edge of blade 20.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention.

What is claimed is:

1. A method of making incisions in a cornea, comprising the steps of:

(a) manipulating an RK knife so that a blade thereof extends a particular depth into the cornea at a starting point;

(b) applying sufficient force to the RK knife to advance the blade in a particular direction;

(c) halting movement of the blade in the particular direction when resistance of the cornea against a leading edge of the blade exceeds a particular level, to thereby complete an incision;

(d) repeating steps (a) through (c) to form a plurality of incisions in a predetermined pattern until a final incision is made wherein resistance of the cornea against the leading edge of the blade exceeds the particular level at the starting point for that final incision; and (e) withdrawing the blade from the cornea, whereby the plurality of incisions reduce strain in collagen fibrils of the cornea so as to correct a refractive error associated with such strain.

2. The method of claim 1 including, for each of the plurality of incisions, detecting a force applied to a body of the RK knife, producing an electrical signal in response to the force, the electrical signal being representative of the amount of the force, and indicating the level of resistance of the cornea against the leading edge of the blade in response to the electrical signal.

3. The method of claim 2 including graphically indicating the level of the resistance on a computer screen in response to the electrical signal.

4. The method of claim 2 including audibly indicating the level of the resistance in response to the electrical signal.

5. The method of claim 1 including supporting the blade on an elastic member and detecting force on the leading edge of the blade by producing the electrical signal to represent an amount of elastic deformation of the elastic member resulting from the force on the leading edge of the blade and indicating the level of resistance of the cornea against the leading edge of the blade in response to the electrical signal.

6. A method of making incisions in a cornea, comprising the steps of:

(a) manipulating an RK knife so that a blade thereof extends a particular depth into the cornea at a starting point;

(b) applying sufficient force to the RK knife to advance the blade in a particular direction;

(c) halting movement of the blade in the particular direction when stria of predetermined prominence are observed on a surface of the cornea immediately ahead of the blade, to thereby complete an incision;

(d) repeating steps (a) through (c) to form a plurality of incisions in a predetermined pattern until a final incision is made wherein resistance of the cornea against the leading edge of the blade exceeds the particular level at the starting point for that final incision; and (e) withdrawing the blade from the cornea, whereby the plurality of incisions relieve strain in collagen fibrils of the cornea so as to correct a refractive error caused by such strain.

7. An apparatus for determining whether strain in fibrils contributing to refractive error in a cornea are in a relaxed condition as a result of prior incisions in the cornea so as to produce an emmetropic or a near emmetropic condition of the cornea, comprising in combination:

(a) an RK knife having a blade adapted to extend a preselected depth into the cornea;

(b) a transducer connected to the RK knife and producing a first electrical signal representative of force applied to the blade to advance it through the cornea;

(c) an analyzing device receiving the first electrical signal, determining if the amount of force exceeds a predetermined resistance level, and if the amount of force exceeds the predetermined resistance level, producing a second electrical signal indicating that the amount of force exceeds the predetermined resistance level; and (d) an indicating device adapted to respond to the second electrical signal to produce information indicating that the amount of force exceeds the predetermined resistance level, whereby when the second electrical signal occurs at a starting point of an incision, the second electrical signal indicates the emmetropic or near emmetropic condition.

8. The apparatus of claim 7 wherein the transducer engages a body of the RK knife and produces the first electrical signal in response to pressure of a surgeon's hand applied against the transducer.

9. The apparatus of claim 7 wherein the indicating device includes a computer adapted to compute the level of the resistance in response to the first electrical signal.

10. The apparatus of claim 7 wherein the transducer includes a strain gauge attached to an elongated elastic member supporting the blade.

11. A method of making incisions in a cornea, comprising the steps of:

(a) manipulating an RK knife so that a blade thereof extends a particular depth into the cornea at a starting point;

(b) applying a force to the RK knife sufficient to advance the blade in a particular direction along the cornea to form an incision;

(c) producing an electrical signal in response to the force, the electrical signal being representative of the amount of the force and thereby being representative of the level of resistance force exerted by the cornea against the blade;

(d) if the force exceeds a predetermined resistance force value, producing an indicating signal indicating that the force exceeds the predetermined resistance force value, halting movement of the blade in the particular direction to thereby complete the incision;

(e) repeating steps (a) through (d) to form a plurality of incisions in a predetermined pattern until a final incision is made wherein resistance of the cornea against the leading edge of the blade exceeds the particular level at the starting point for that final incision; and (e) withdrawing the blade from the cornea, whereby the plurality of incisions relieve strain in collagen fibrils of the cornea so as to correct a refractive error caused by such strain.

12. The method of claim 11 including, for each of the plurality of incisions, producing audible information in response to the indicating signal, step (d) including terminating that incision in response to the audible information.

13. The method of claim 11 including, for each of the plurality of incisions, producing graphic information in response to the indicating signal, step (d) including terminating that incision in response to the graphic information.

14. A method of determining an end point of procedure for correcting a refractive error of a cornea, comprising the steps of:

(a) performing a fibril strain reducing procedure on a portion of the cornea, the fibril strain reducing procedure resulting in reducing strain in fibrils therein which are under increased strain associated with the refractive error;

(b) measuring a property of the cornea indicative of strain in corneal collagen fibrils in the portion of the cornea; and (c) terminating the fibril strain reducing procedure after the measurement indicates that the strain in the fibrils in the portion of the cornea is below a predetermined level.

* * * * *